United States Patent
Tsuruta et al.

(10) Patent No.: US 10,040,743 B2
(45) Date of Patent: Aug. 7, 2018

(54) METHOD FOR PRODUCING ALDEHYDE COMPOUND, AND ACETAL COMPOUND

(71) Applicant: KURARAY CO., LTD., Kurashiki-shi (JP)

(72) Inventors: Takuo Tsuruta, Kamisu (JP); Ryosuke Shimizu, Tainai (JP); Takahiro Hosono, Tainai (JP); Naoya Minamoto, Tainai (JP)

(73) Assignee: KURARAY CO., LTD., Kurashiki-shi (JP)

( * ) Notice: Subject to any disclaimer, the term of this patent is extended or adjusted under 35 U.S.C. 154(b) by 0 days.

(21) Appl. No.: 15/538,443

(22) PCT Filed: Dec. 17, 2015

(86) PCT No.: PCT/JP2015/085384
§ 371 (c)(1),
(2) Date: Jun. 21, 2017

(87) PCT Pub. No.: WO2016/104332
PCT Pub. Date: Jun. 30, 2016

(65) Prior Publication Data
US 2017/0369411 A1    Dec. 28, 2017

(30) Foreign Application Priority Data
Dec. 24, 2014   (JP) .................... 2014-261082

(51) Int. Cl.
| C07C 45/42 | (2006.01) |
| C07C 45/39 | (2006.01) |
| C07C 45/59 | (2006.01) |
| C07C 47/12 | (2006.01) |
| C07D 317/12 | (2006.01) |

(52) U.S. Cl.
CPC .............. *C07C 45/42* (2013.01); *C07C 45/59* (2013.01); *C07C 47/12* (2013.01); *C07D 317/12* (2013.01)

(58) Field of Classification Search
CPC ......... C07C 45/42; C07C 45/39; C07C 47/12; C07D 317/12
See application file for complete search history.

(56) References Cited

U.S. PATENT DOCUMENTS

| 4,256,643 A | 3/1981 | Jaedicke et al. |
| 4,608,443 A | 8/1986 | Andrade et al. |
| 4,675,451 A | 6/1987 | Andrade et al. |
| 2003/0089885 A1 | 5/2003 | Rogers et al. |

FOREIGN PATENT DOCUMENTS

| DE | 2137603 | 2/1973 |
| JP | 55-49373 A | 4/1980 |
| JP | 60-188341 A | 9/1985 |
| JP | 61-194043 A | 8/1986 |
| JP | 7-281342 A | 10/1995 |
| JP | 2009-102244 A | 5/2009 |
| WO | 02/085294 A2 | 10/2002 |

OTHER PUBLICATIONS

G. D. Cuny, et al., "Practical, High-Yield, Regioselective, Rhodium-Catalyzed Hydroformylation of Functionalized α-Olefins," Journal of the American Chemical Society, 1993, vol. 115, 1 page.
"3,4-Dihydro-2-Methoxy-4-Methyl-2H-Pyran," Organic Syntheses, Cell, vol. 4, p. 311 (1963); vol. 34, p. 29 (1954), (Total 2 Pages).
"3-Methyl-1,5-Pentanediol," Organic Syntheses Coll, vol. 4, p. 660 (1963), vol. 34, p. 71 (1954), (Total 3 Pages).
International Search Report dated Feb. 16, 2016 in PCT/JP2015/085384 filed Dec. 17, 2015.

*Primary Examiner* — Sikarl A Witherspoon
(74) *Attorney, Agent, or Firm* — Oblon, McClelland, Maier & Neustadt, L.L.P.

(57) ABSTRACT

Provided are a method for producing 3-methylglutaraldehyde in a good yield under a mild condition and a novel acetal compound which is useful for carrying out the foregoing method. The method is a production method of 3-methylglutaraldehyde including a step of hydrolyzing a compound represented by the following general formula (1):

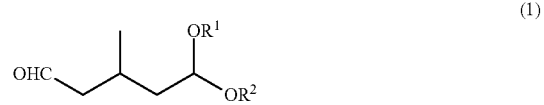

(1)

wherein $R^1$ and $R^2$ each independently represent an alkyl group having 1 to 6 carbon atoms, or are mutually coupled to represent an alkylene group having 2 to 6 carbon atoms.

5 Claims, No Drawings

METHOD FOR PRODUCING ALDEHYDE COMPOUND, AND ACETAL COMPOUND

TECHNICAL FIELD

The present invention relates a production method of 3-methylglutaraldehyde an a acetal compound.

BACKGROUND ART

3-Methylglutaraldehyde 3-methyl-1,5-pentanedial, hereinafter abbreviated as "MGL") is a useful compound as a curing gent for photosensitive material, a tanning agent or leather, and a synthesis intermediate (see, for example, PTLs 1 to 3). As a production method of MGL, a method of hydrolyzing pyranyl ether which is obtained by the Diels-Alder reaction between croton aldehyde and methyl vinyl ether is known (see NPLs 1 and 2).

CITATION LIST

Patent Literature

PTL 1: JP 07-281342 A
PTL 2: DE 2137603 A
PTL 3: JP 2600-10224 A

Non-Patent Literature

NPL 1: *Organic Syntheses*, Vol. 34, p.29 (1954)
NPL 2: *Organic Syntheses*, Vol. 34, p.71 (1954)

SUMMARY OF INVENTION

Technical Problem

According to the aforementioned conventional methods, the reactivity of the Diels-Alder reaction between croton aldehyde and methyl vinyl ether is low, a severe condition of high temperature and high pressure is required, and the yield of MGL is low. Thus, there was room for improvement. In consequence, an object of the present invention is to provide a method for producing MGL in a good yield under a mild condition and a novel acetal compound which is useful for carrying out the foregoing method.

Solution to Problem

In accordance with the present invention, the aforementioned object is achieved by the following [1] to [3].

[1] A production method of 3-methylglutaraldehyde, including a step of hydrolyzing a compound represented by the following general formula (1) (hereinafter referred to as "acetal compound (1)"):

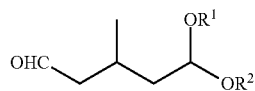
(1)

wherein $R^1$ and $R^2$ each independently represent an alkyl group having 1 to 6 carbon atoms, or are mutually coupled to represent an alkylene group having 2 to 6 carbon atoms.

[2] The production method according to [1], further including a step of subjecting a compound represented by the following general formula (2) (hereinafter referred to as "acetal compound (2)"):

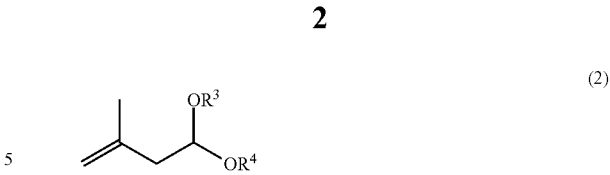
(2)

wherein $R^3$ and $R^4$ each independently represent an alkyl group having 1 to 6 carbon atoms, or are mutually coupled to represent an alkylene group having 2 to 6 carbon atoms, to hydroformylation to obtain the acetal compound (1).

[3] A compound represented by the following general formula (3) (hereinafter referred to as "acetal compound (3)"):

(3)

wherein $R^5$ represents a linear alkylene group having 2 to 6 carbon atoms.

Advantageous Effects of Invention

In accordance with the present invention, a method for producing MGL a good yield under a mild condition and a novel acetal compound which is useful for carrying out the foregoing method are provided.

DESCRIPTION OF EMBODIMENTS

In the present invention, MGL is produced through hydrolysis of the acetal compound (1).

The acetal compound (1) can be suitably produced through a hydroformylation reaction of the acetal compound (2).

In the acetal compound (1) and the acetal compound (2), the alkyl group having 1 to 6 carbon atoms, as represented by $R^1$ to $R^4$, may be linear, branched, or cyclic, and examples thereof include a methyl group, an ethyl group, an n-propyl group, an isopropyl group, an n-butyl group, an isobutyl group, a butyl group, an n-pentyl group, a cyclohexyl group, and the like. Above all, a methyl group, an ethyl group, and an n-propyl group are preferred, and a methyl group and an ethyl group are more preferred.

Examples of the alkylene group which $R^1$ and $R^2$, or $R^3$ and $R^4$, are mutually coupled to form include an ethylene group, an n-propylene group, an n-butylene group, an n-pentylene group, an n-hexylene group, a 2-methylethylene group, a 1,2-dimethylethylene group, a 2-methyl-n-pentylene group, a 2,2-dimethyl-n-propylene group, a 3-methyl-n-pentylene group, and the like. Above all, an ethylene group, an n-propylene group, a 2-methyl-n-propylene group, a 2,2-dimethyl-n-propylene group, a 2-methylethylene group, and a 1,2-dimethylethylene group are preferred; an ethylene group, n-propylene group, a 2-methyl-n-propylene group, and a 2,2-dimethyl-n-propylene group are more preferred; and an ethylene group and an n-propylene group are especially preferred.

(Production of Acetal Compound (2))

The production method of the acetal compound (2) is not limited, and examples thereof include a method of subjecting 3-methyl-3-buten-1-al to acetalization in the presence of an alcohol corresponding to the aforementioned $R^1$ to $R^4$. Here, the 3-methyl-3-buten-1-al to be used can be synthesized from isoprenol according to a method described in, for example, JP 2007-525522 A or WO 08/037693 A.

Though the acetalization reaction is advanced even in the absence of a catalyst, an acid catalyst may be used, if desired. The acid to be used is not particularly limited, and examples thereof include inorganic acids and salts thereof, such as sulfuric acid, phosphoric acid, nitric acid, hydrochloric acid, boric acid, etc.; organic acids and salts thereof, such as formic acid, acetic acid, propionic acid, oxalic acid, methanesulfonic acid, p-toluenesulfonic acid, pyridinium p-toluenesulfonate, etc.; solid acids, such as a cation exchange resin, silica alumina, zeolite, activated clay, etc.; and the like.

Though the use amount of the aforementioned catalyst varies with the kind of the acid used or the amount of water, so far as the case of using hydrochloric acid is concerned, the catalyst is used in an amount of preferably ranging from 0.00001% by mass to 10% by mass, and more preferably ranging from 0.0001% by mass to 5% by mass of the reaction solution as expressed in terms of the hydrogen chloride molecule. When the use amount of the catalyst is less than 0.00001% by mass, a sufficient reaction rate is often not obtained, whereas in the case of using the catalyst in an amount of more than 10% by mass, the use amount of a base on the occasion of neutralization increases, so that a load in a post-treatment process increases.

It is possible to carry out the acetalization reaction by all of batch and continuous methods. In addition, a mode of extracting water produced on the conversion of 3-methyl-3-buten-1-al into the acetal compound (2) to the outside of the system simultaneously with the reaction can also be adopted. After the reaction, if desired, the acid catalyst can be removed and used for a next reaction, or the acetal compound (2) may be purified by a usual purification method, such as distillation, etc.

Among the acetal compounds (2), in view of the fact that the production is easy, the following acetal compound (3):

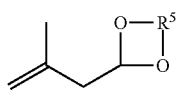
(3)

wherein $R^5$ represents a linear alkylene group having 2 to 6 carbon atoms, is especially preferred. Incidentally, such an acetal compound (3) is a novel compound.

(Production of Acetal Compound (1))

The acetal compound (1) is suitably obtained by a method of subjecting the acetal compound (2) to hydroformylation.

The hydroformylation reaction is performed by allowing the acetal compound (2) to react with carbon monoxide and hydrogen in the presence of a metal compound belonging to the Groups 8 to 10 and if desired, a ligand.

Examples of the metal compound belonging to the Groups 8 to 10 include a rhodium compound, a cobalt compound, a ruthenium compound, an iron compound, and the like. Examples of the rhodium compound include Rh(acac)(CO)$_2$, Rh(acac)$_3$, RhCl(CO)(PPh$_3$)$_2$, RhCl(PPh$_3$)$_3$, RhBr(CO)(PPh$_3$)$_2$, Rh$_4$(CO)$_{12}$, Rh$_6$(CO)$_{16}$, and the like. Examples of the cobalt compound include HCo(CO)$_3$, HCo(CO)$_4$, Co$_2$(CO)$_8$, HCo$_3$(CO)$_8$, and the like. Examples of the ruthenium compound include Ru(CO)$_3$(PPh$_3$)$_2$, RuCl$_2$(PPh$_3$)$_3$, RuCl$_3$(PPh$_3$)$_8$, Ru$_3$(CO)$_{12}$, and the like. In addition, examples of the iron compound include Fe(CO)$_5$, Fe(CO)$_4$PPh$_3$, Fe(CO)$_4$(PPh$_3$)$_2$, and the like. Among them, it is preferred to use the rhodium compound in which a comparatively mild reaction condition is readily selected, and from the viewpoint of easiness of availability, it is especially preferred to use Rh(acac)(CO)$_2$ and Rh(acac)$_3$.

The use amount of the metal compound belonging to the Groups 8 to 10 is preferably in a range of 0.0001 to 100 mmol, and more preferably in a range of 0.005 to 10 mmol as expressed in terms of a metal atom per liter of the reaction mixture. When the use amount of the metal compound belonging to the Groups 8 to 10 is less than 0.0001 mmol as expressed in terms of a metal atom per liter of the reaction mixture, the reaction rate tends to become extremely slow, whereas even when it is more than 100 mmol, an effect corresponding thereto is not obtained, and the catalyst costs merely increase.

The ligand to be used is not particularly limited, and conventionally known ligands can be used. Examples of such a ligand which can be used include compounds represented by the following general formulae (4) to (6); phosphoramidites (see WO 03/018192 A, WO 02/083695 A, WO 04/026803 A, WO 06/045597 A, WO 03/08642 A, WO 00/005641 A, WO 99/65606 A, and WO 99/46044 A); phosphites having a specified crosslinking structure (see WO 95/00525 A and WO 01/58589 A); phosphines having a specified substituent (see WO 03/053571 A, WO 03/053572 A, WO 09/059963 A, and WO 00/69801 A); phosphabenzene (see WO 97/46507 A and WO 00/55164 A); phosphines having a specified crosslinking structure (see WO 01/85661 A); and the like.

Specifically, for example, compounds described on pages 9 to 40 of JP 2007-506691 A can be used.

The ligands may be used alone, or may be used in combination of two or more thereof.

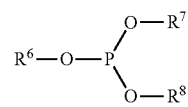
(4)

Here, to $R^6$ to $R^8$ each independently represent an optionally substituted hydrocarbon group having 1 to 24 carbon atoms, and may be mutually coupled.

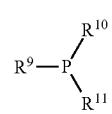
(5)

Here, $R^9$ to $R^{11}$ each independently represent an optionally substituted hydrocarbon group having 1 to 24 carbon atoms, and may be mutually coupled.

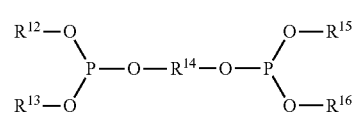
(6)

Here, $R^{12}$, $R^{13}$, $R^{15}$ and $R^{16}$ each independently represent an optionally substituted hydrocarbon group having 1 to 40 carbon atoms, and $R^{12}$ and $R^{13}$ or $R^{15}$ and $R^{16}$, may be mutually coupled; and $R^{14}$ represents an optimally substituted hydrocarbon crosslinking group having 1 to 40 carbon atoms.

In the foregoing general formula (4) and general formula (5), the optionally substituted hydrocarbon group having 1 to 24 carbon atoms, which $R^6$ to $R^{11}$ each independently represent, may be linear, branched, or cyclic, and examples thereof include an alkyl group, such as a methyl group, an ethyl group, an n-propyl group, an isopropyl group, an n-butyl group, an isobutyl group, a t-butyl group, an n-pentyl group, a cyclohexyl group, etc.; an aryl group, such as a phenyl group, a naphthyl group, an anthracenyl group, etc.; and the like. Above all, a phenyl group and a naphthyl group are preferred.

The aforementioned hydrocarbon group may have any substituent so long as the hydroformylation reaction is not impaired, and examples thereof include an alkyl group, an aryl group, an alkoxy group, a silyl group, an amino group, an acyl group, a carboxy group, an acyloxy group, an amide group, an ionic group, such as —$SO_3M$ (wherein M represents an inorganic or organic cation), etc., a sulfonyl group, a halogen, a nitro group, a cyano group, a fluoroalkyl group, a hydroxy group, and the like.

Examples of the compound represented by the general formula (4), which is used as the ligand in the present invention, include tris(2-methylphenyl) phosphite, tris(2,6-dimethylphenyl) phosphite, tris(2-isopropyphenyl) phosphite, tris(2-phenylphenyl) phosphite, tris(2-t-butylphenyl) phosphite, tris(2-t-butyl-5-methylphenyl) phosphite, tris(2,4-di-t-butylphenyl) phosphite, di(2-methylphenyl)(2-t-butylphenyl) phosphite, di(2-t-butylphenyl)(2-methylphenyl) phosphite, and the like, but the compound is not limited thereto. Above all, tris(2-t-butylphenyl) phosphite, tris(2-t-butyl-5-methylphenyl) phosphite, and tris(2,4-di-t-butylphenyl) phosphite are preferred from the standpoint of industrially carrying out the present invention.

In the general formula (4), specific examples of the compound in which $R^6$ to $R^8$ are mutually coupled are exemplified below, but the compound is not limited thereto.

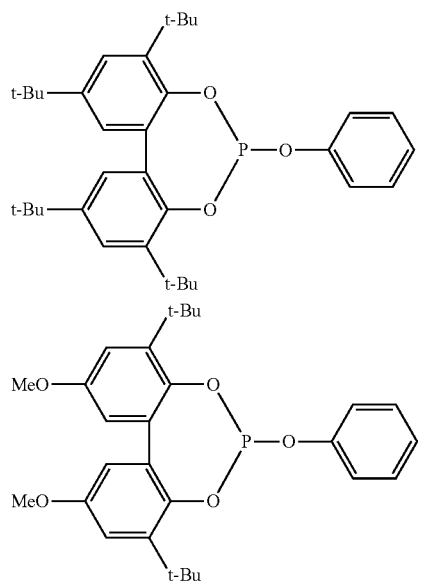

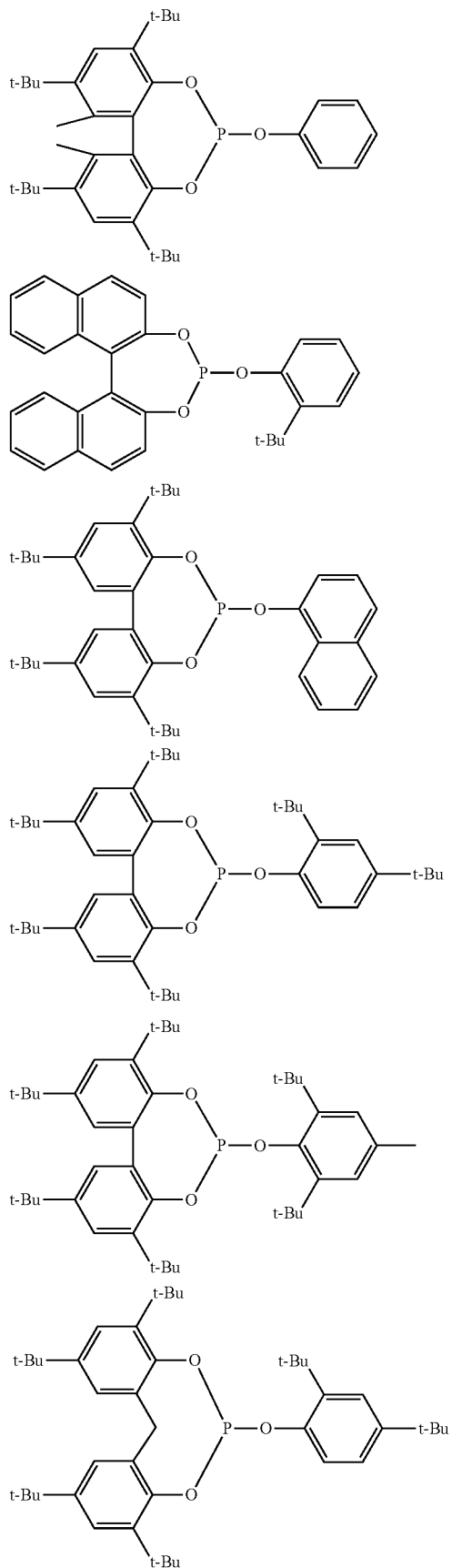

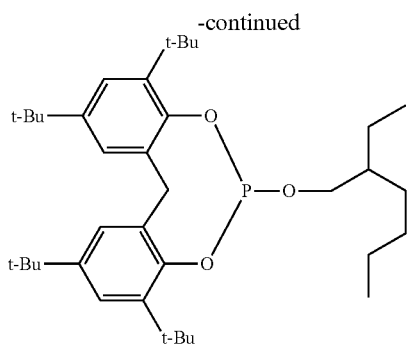

Examples of the compound represented by the general formula (5), which is used as the ligand in the present invention, include triphenylphosphine, tri(p-tolyl)phosphine, tri(p-methoxyphenyl)phosphine, tri(p-fluorophenyl)phosphine, tri(p-chlorophenyl)phosphine, tri(dimethylaminophenyl)phosphine, propyldiphenylphosphine, t-butyldiphenylphosphine, n-butyldiphenylphosphine, n-hexyldiphenylphosphine, cyclohexyldiphenylphosphine, dicyclohexylphenylphosphine, tricyclohexylphosphine, tribenzylphosphine, sulfonated triphenylphosphine, alkali metal salts and alkaline earth metal salts of (tri-m-sulfonyl)phosphine and (m-sulfonyl)diphenylphosphine, etc., and the like, but the compound is not limited thereto.

Among the compounds represented by the general formulae (4) and (5), those falling within such a range that the electronic parameter (ν-values) is 2,080 to 2,090 cm$^{-1}$, and the steric parameter (θ-values) is 135 to 190° are preferred. The aforementioned two kinds of parameters are values defined according to the description of a literature [C. A. Tolman, *Chem. Rev.*, 177, 313 (1977)]. The electronic parameter is one defined in terms of a frequency of A1 infrared absorption spectrum of CO of Ni(CO)$_3$L (L is a phosphorus ligand) as measured in dichloromethane; and the steric parameter is defined in terms of a vertex angle of cone drawn so as to surround the van der Waals radius of an atom existent in the outermost of a group bonding to phosphorus at a position of 2.28 angstrom from the center of the phosphorus atom.

In the foregoing general formula (6), the optionally substituted hydrocarbon group having 1 to 40 carbon atoms, which $R^{12}$, $R^{13}$, $R^{15}$, and $R^{16}$ each independently represent, may be linear, branched, or cyclic, and examples thereof include an alkyl group, such as a methyl group, an ethyl group, an n-propyl group, an isopropyl group, an n-butyl group, an isobutyl group, a t-butyl group, as n-pentyl group, a cyclohexyl group, etc.; and an aryl group, such as a phenyl group, a naphthyl group, an anthracenyl group etc. Above all, a phenyl group and a naphthyl group are preferred.

The aforementioned hydrocarbon group may have any substituent so long as the hydroformylation reaction is not impaired, and examples thereof include an alkyl group, an aryl group, an alkoxy group, a silyl group, n amino group, an acyl group, a carboxy group, an acyloxy group, amide group, an ionic group, such as —SO$_3$M (wherein M represents an inorganic or organic cation), etc., a sulfonyl group, a halogen, a nitro group, a cyano group, a fluoroalkyl group, a hydroxy group, and the like.

As $R^{12}$ and $R^{13}$ which are mutually coupled, $R^{15}$ and $R^{16}$ which are mutually coupled, and $R^{14}$, there are exemplified an alkylene group, a cycloalkylene group, a phenylene group, a naphthylene group, a divalent crosslinking group represented by the following general formula (7), and the like.

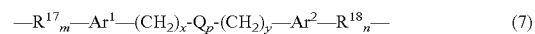

Here, $R^{17}$ and $R^{18}$ each independently represent an optionally substituted alkylene group having 1 to 6 carbon atoms; Ar$^1$ and Ar$^2$ each independently represent an optionally substituted arylene group; in, n, p, x, and y each represent 0 or 1; Q represents a divalent crosslinking group selected from —CR$^{19}$R$^{20}$—, —O—, —S—, —NR$^{21}$—, —SiR$^{22}$R$^{23}$—, and —CO—; and $R^{19}$ to $R^{23}$ each independently represent any one of hydrogen, an optionally substituted alkyl group having 1 to 12 carbon atoms, a phenyl group, a tolyl group, and an anisyl group.

Examples of the alkylene group include an ethylene group, a trimethylene group, a tetramethylene group, a pentamethylene group, groups represented by the following formulae, and the like.

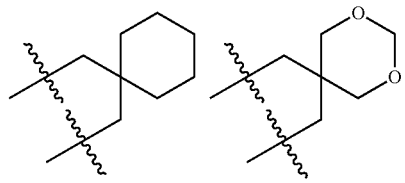

In the formulae, the broken line represents a coupling site.

Examples of the cycloalkylene group include a cyclopropylene group, a 1,2-cyclopentylene group, a 1,3-cyclopentylene group, a 1,2-cyclohexylene group, a 1,3-cyclohexylene group, a 1,4-cyclohexylene group, and the like.

Examples of the phenylene group include a 1,2-phenylene group, a 1,3-phenylene group, a 1,4-phenylene group, and the like.

Examples of the naphthylene group include a 1,2-naphthylene group, a 1,8-naphthylene group, and the like.

All of $R^{12}$ and $R^{13}$ which are mutually coupled, $R^{15}$ and $R^{16}$ which are mutually coupled, and $R^{14}$ may have a substituent. Examples of such a substituent include an alkyl group preferably having 1 to 5 carbon atoms, such as a methyl group, an ethyl group, a propyl group, a butyl group, a pentyl group etc.; an alkoxyl group preferably having 1 to 4 carbon atoms, such as a methoxy group an ethoxy group, a propoxy group, a butoxy group, etc.; an aryl group, such as a phenyl group, a naphthyl group, etc.; and the like.

In the general formula (7), examples of the optionally substituted alkylene group having 1 to 6 carbon, atoms, as represented by $R^{17}$ and $R^{18}$, include an ethylene group, an n-propylene group, an n-butylene group, an n-pentylene group, an n-hexylene group, a 2-methyl-ethylene group, a 1,2-dimethylethylene group, a 2-methyl-n-propylene group, a 2,2-dimethyl-n-propylene group, a 3-methyl-n-pentylene group, and the like. Examples of the arylene group represented by Ar$^1$ and Ar$^2$ include a phenylene group, a naphthylene group, an anthracenylene group, and the like. Examples of the optionally substituted alkyl group having 1 to 12 carbon atoms, as represented by $R^{19}$ to $R^{23}$, include a methyl group, an ethyl group, an n-propyl group, isopropyl group, an n-butyl group, an isobutyl group, a t-butyl group an n-pentyl group, and a cyclohexyl group.

Each of $R^{17}$ to $R^{23}$, Ar$^1$, and Ar$^2$ may have any substituent so long as the hydroformylation reaction is not impaired, and examples thereof include an alkyl group, an aryl group, an alkoxy group, a silyl group, an amino group, an acyl group, a carboxy group, an acyloxy group, an amide group, ionic group, such as —SO$_3$M (wherein M represents an inorganic or organic cation), etc., a sulfonyl group, a halogen, a nitro group, a cyano group, a fluoroalkyl group, a hydroxy group, and the like.
Examples of the compound represented by the general formula (6) include the following compounds, but the compound is not limited thereto.
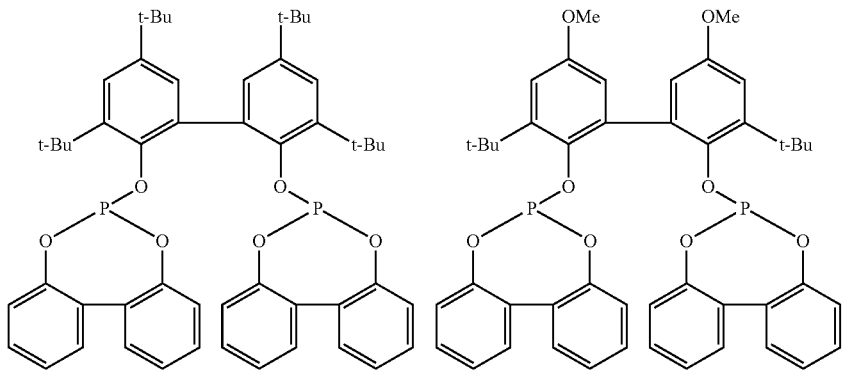
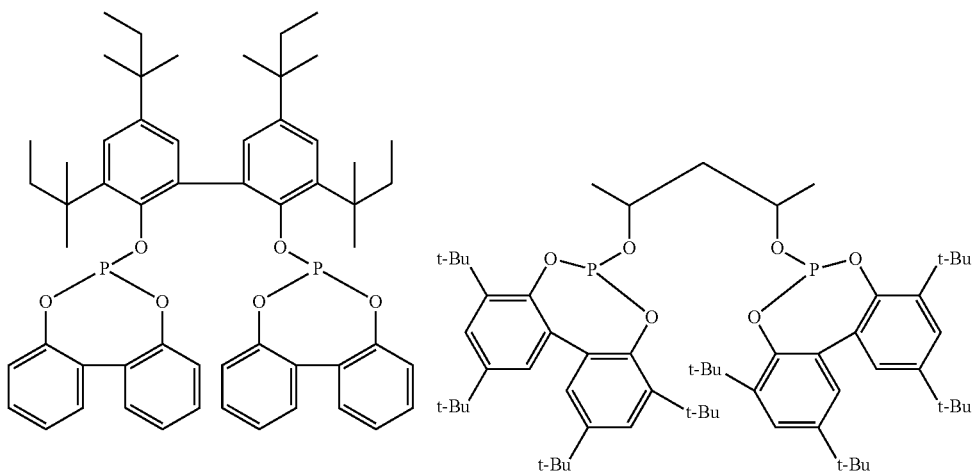
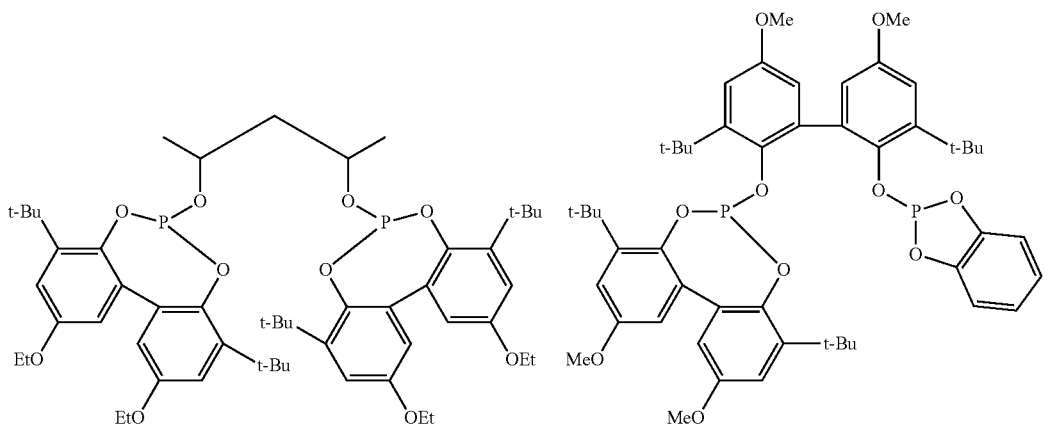

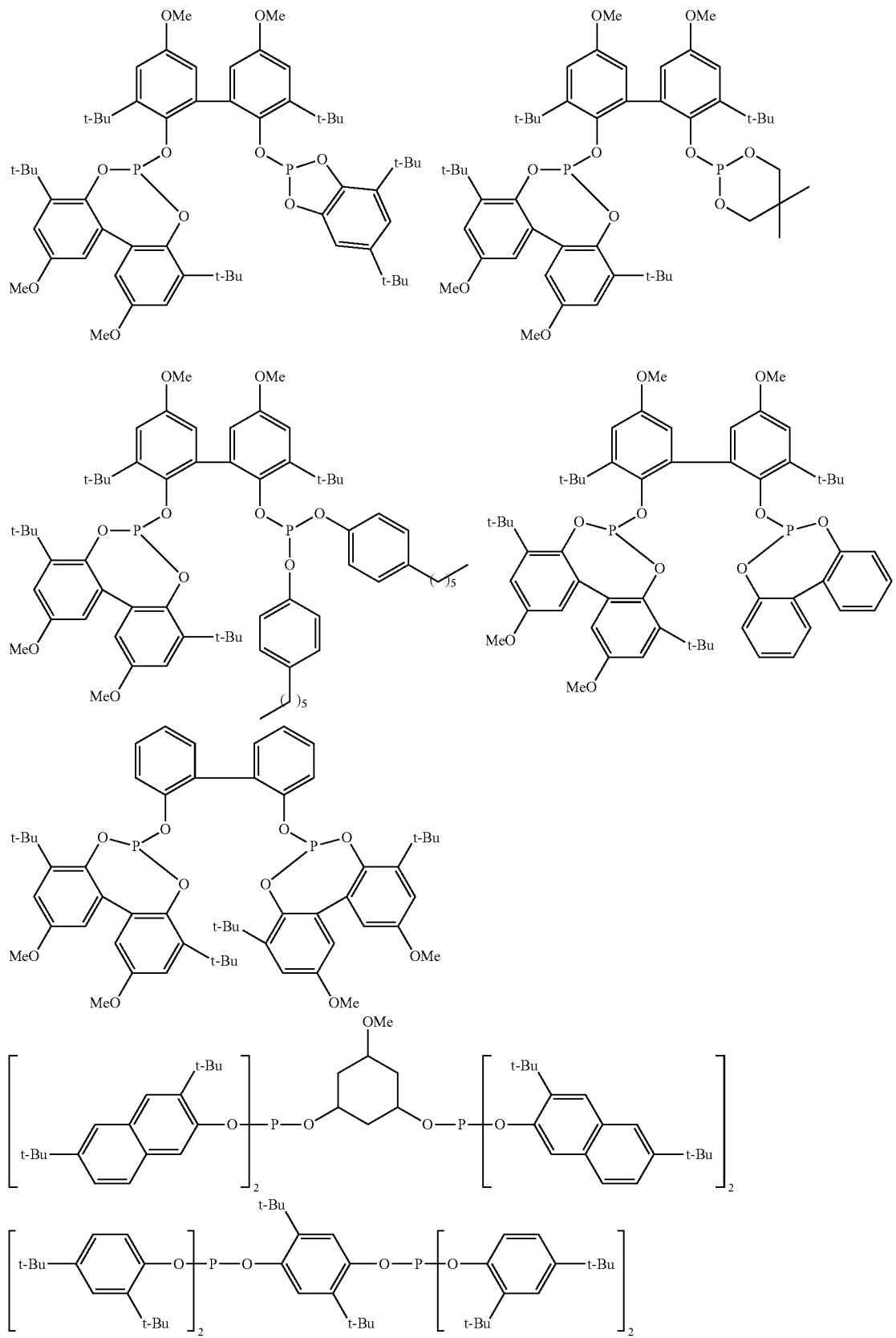

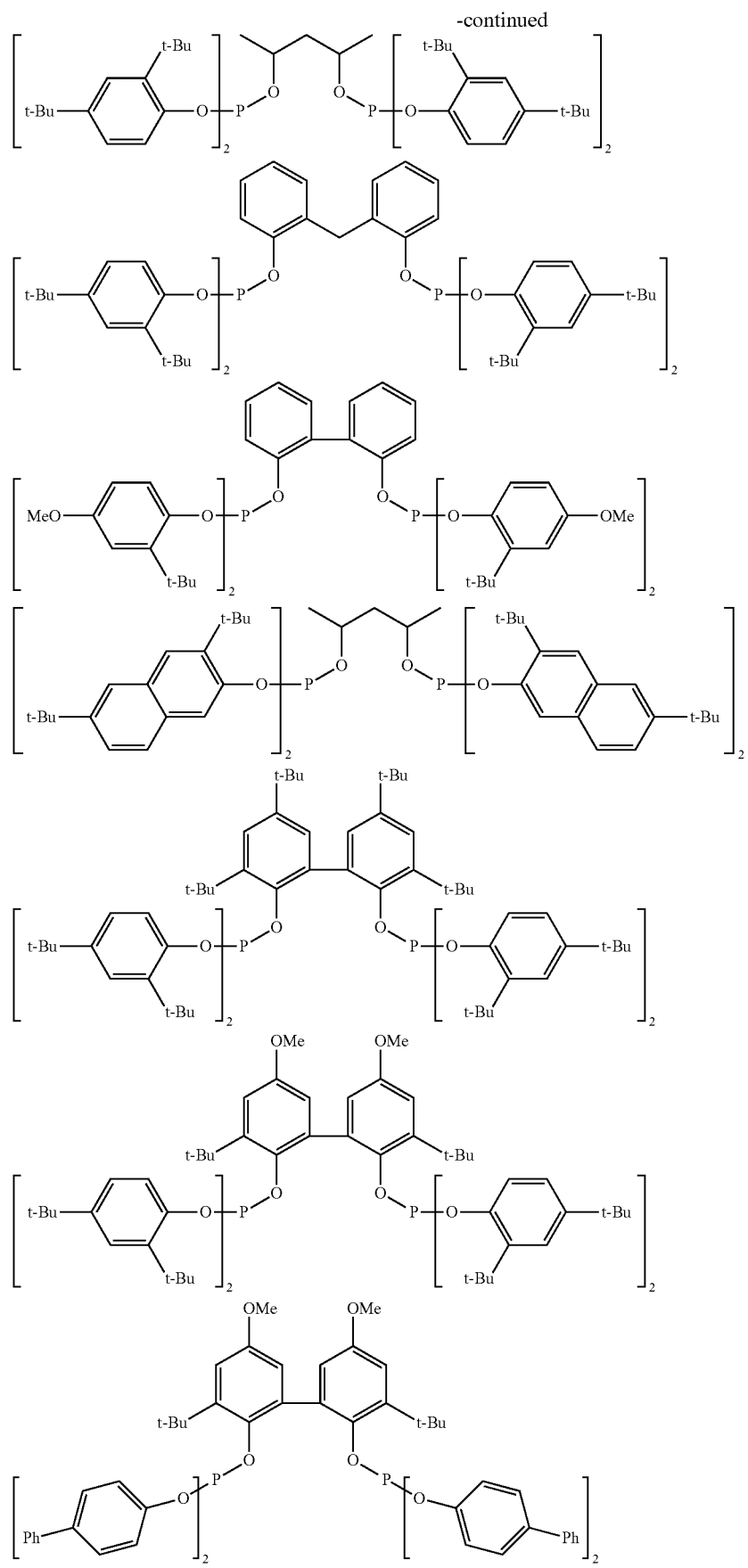

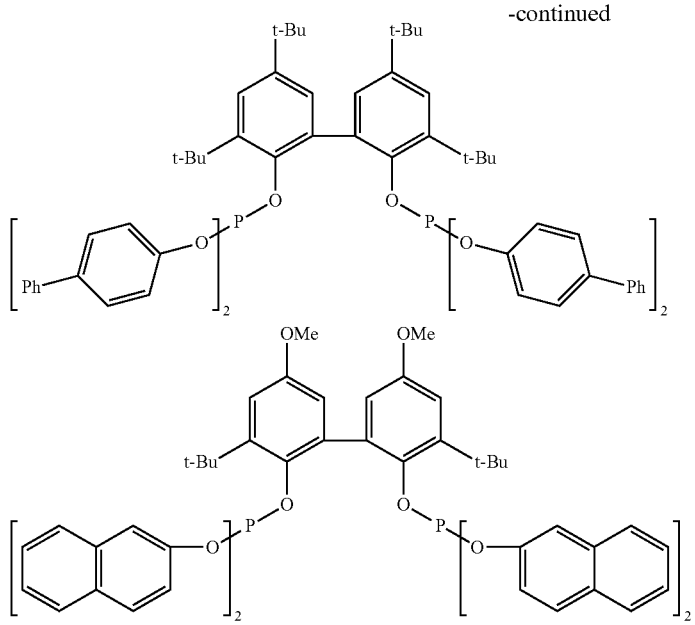
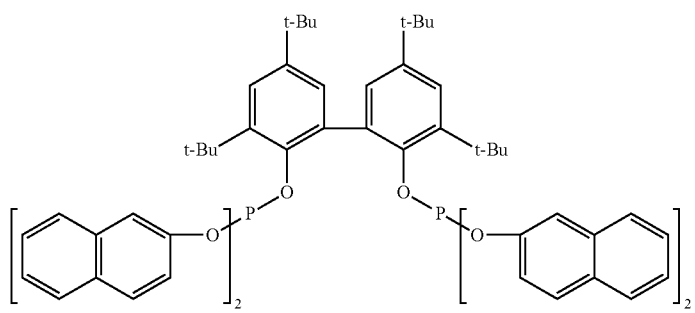
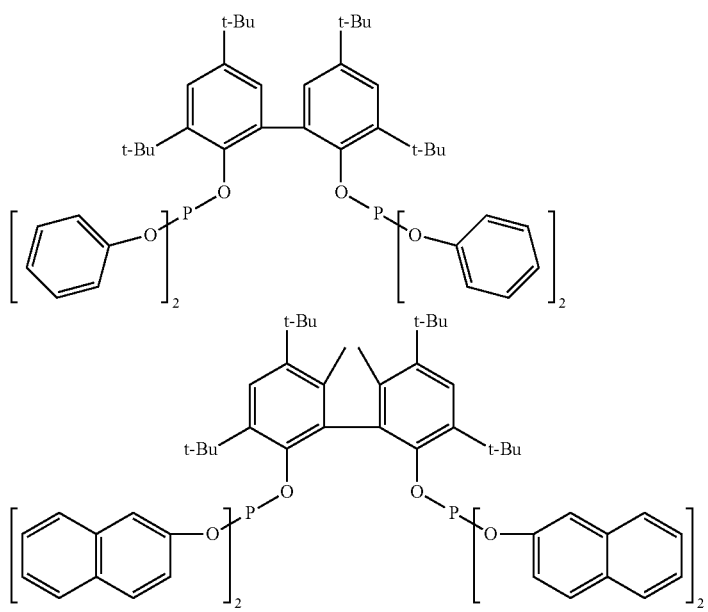

-continued
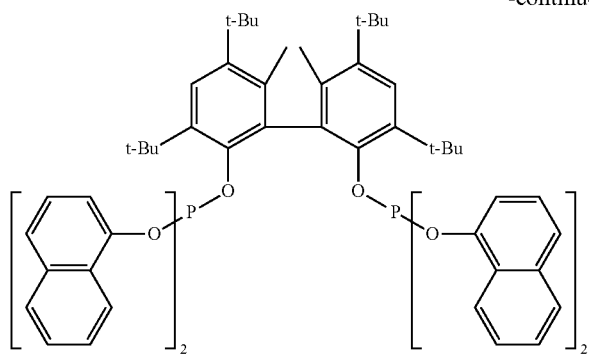
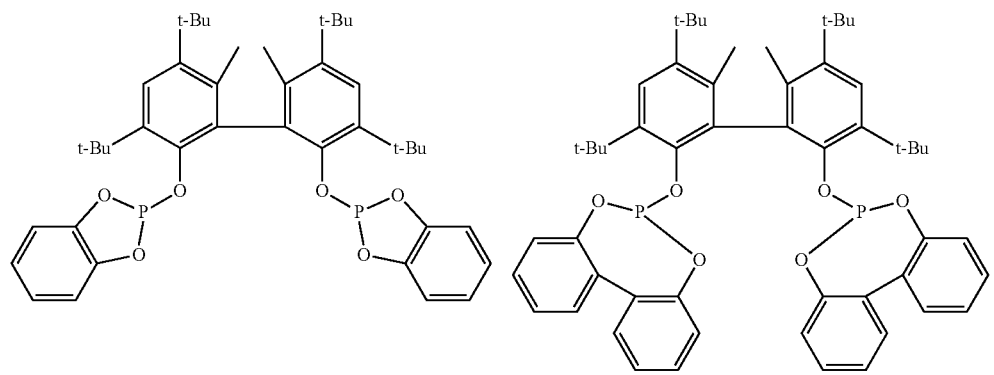
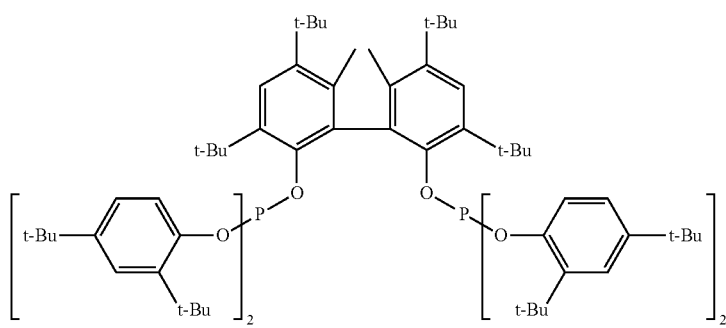
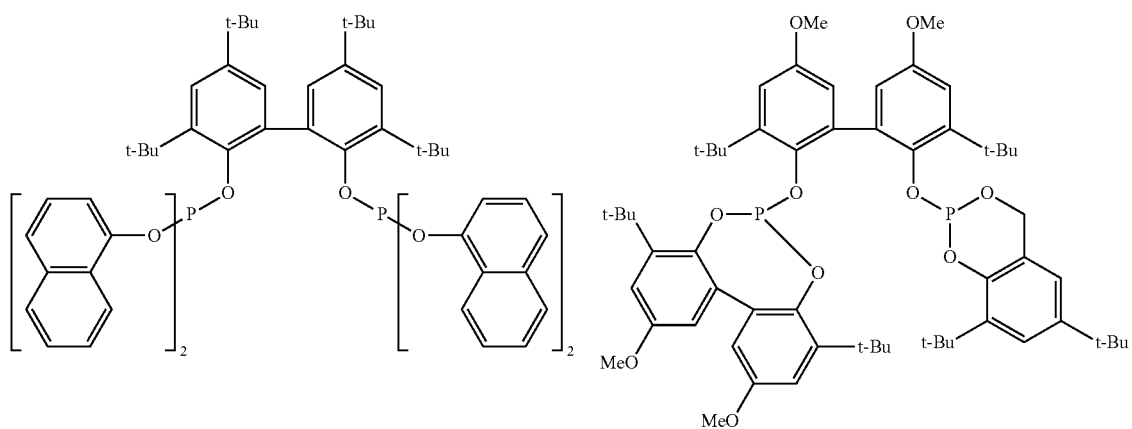

19
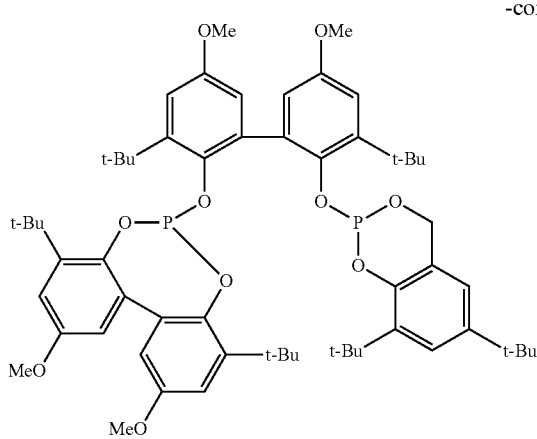
20
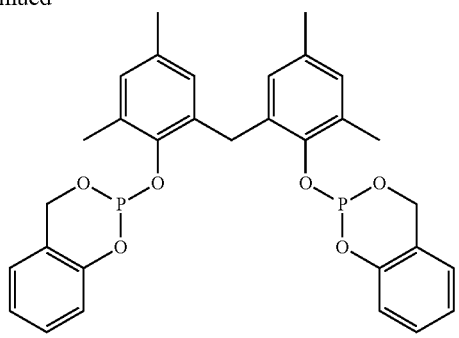
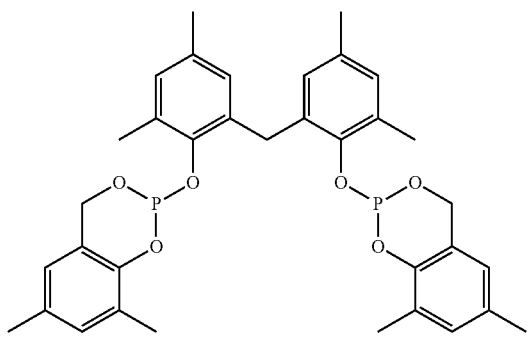
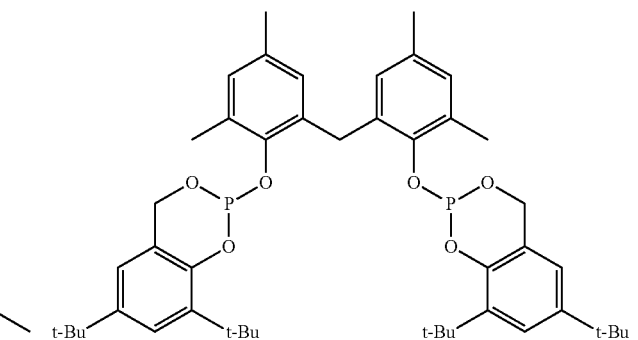
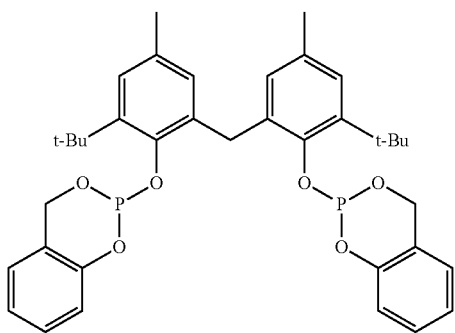
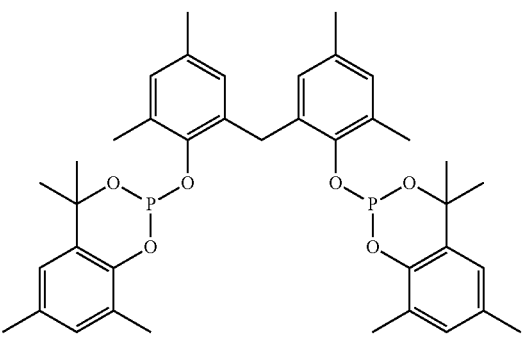
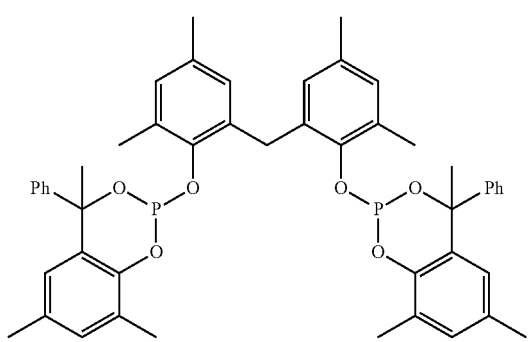
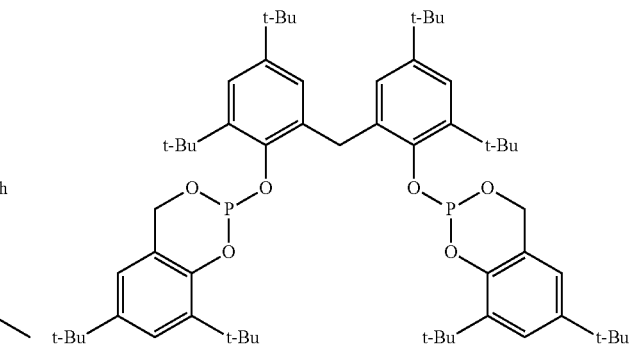

21
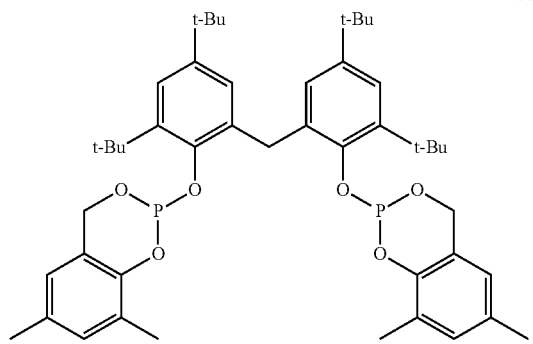
22
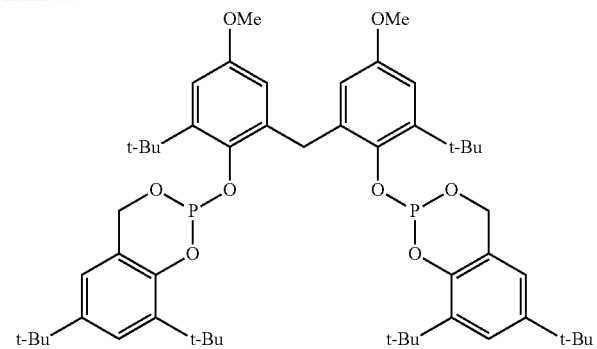
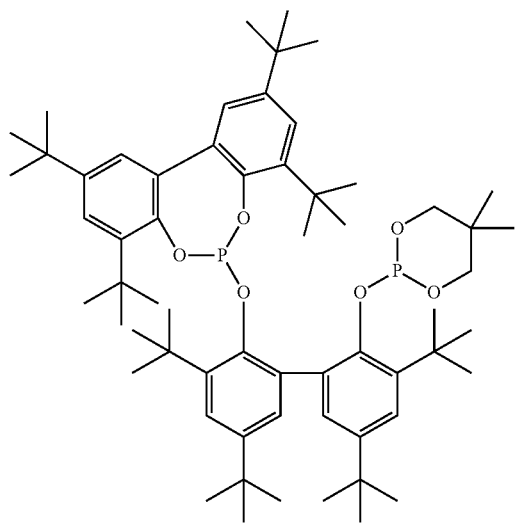
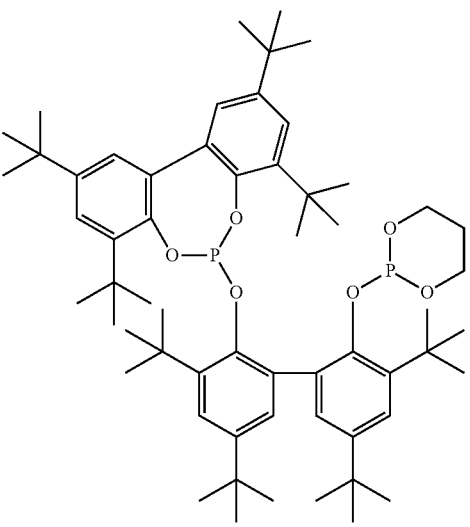
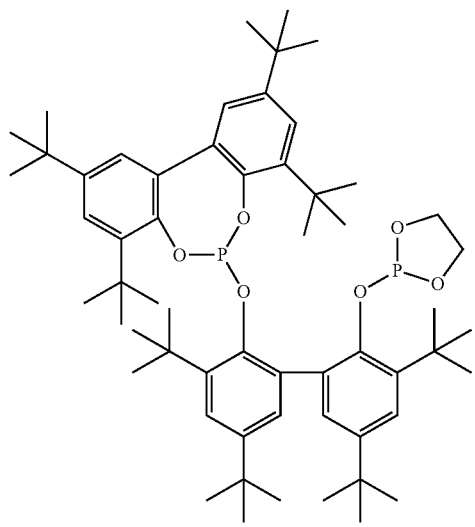
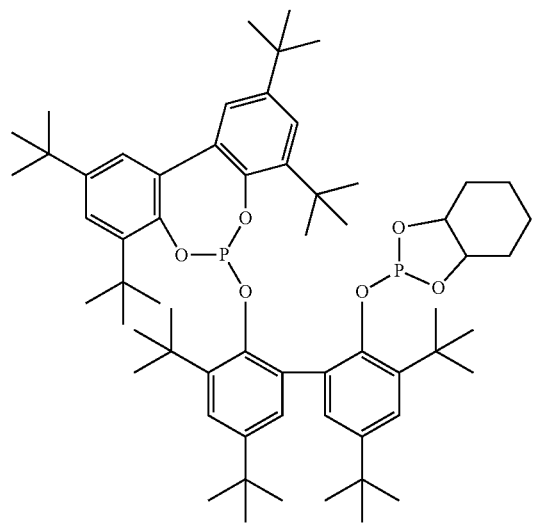

-continued
23
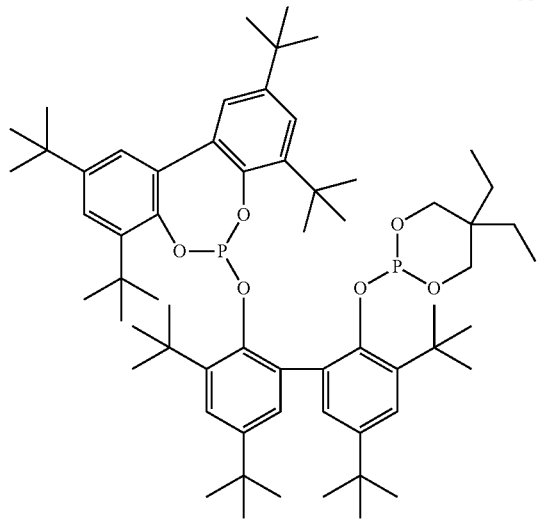
24
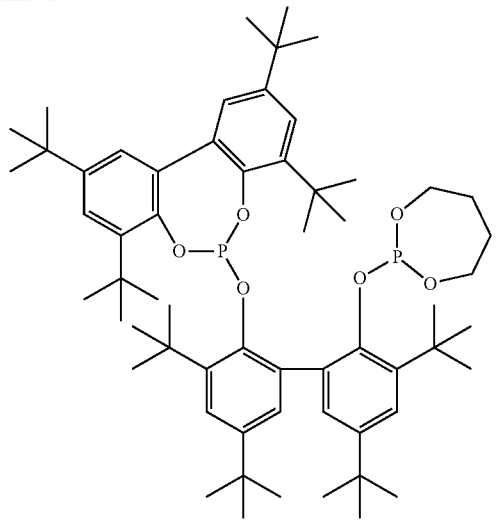
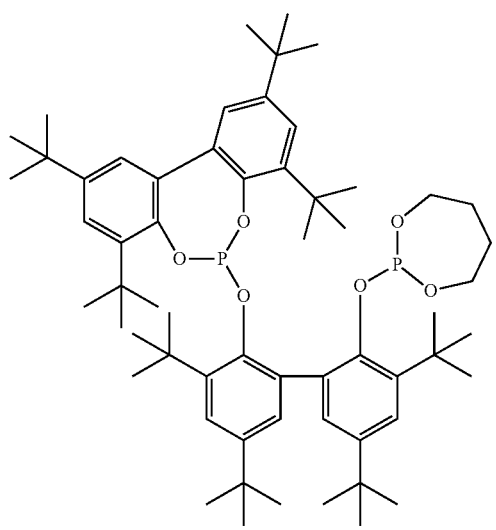
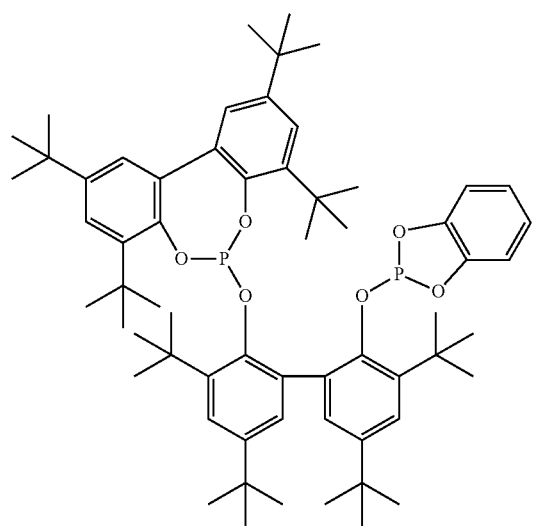
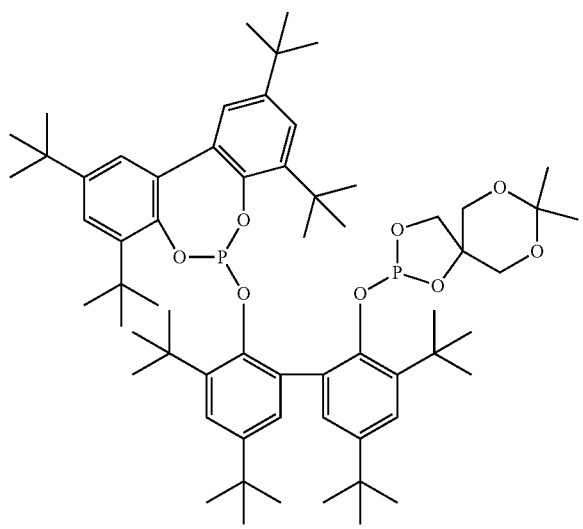

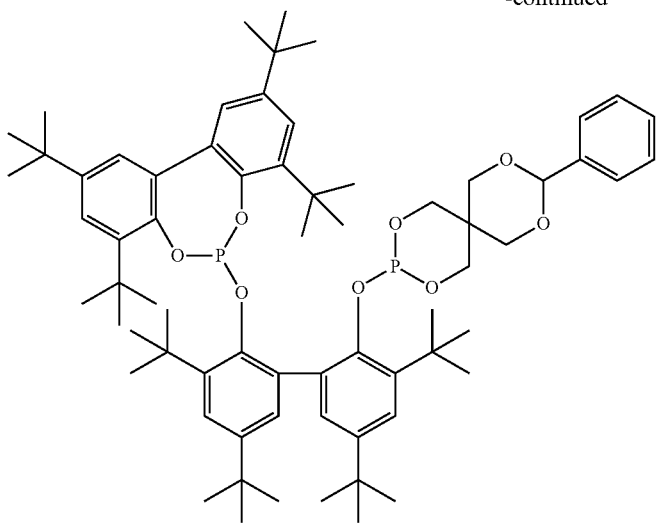
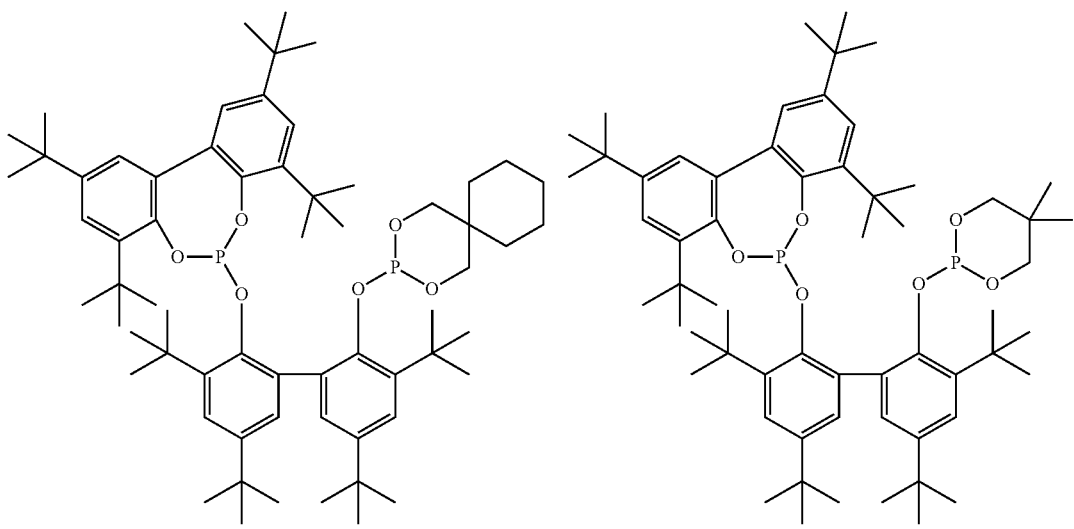
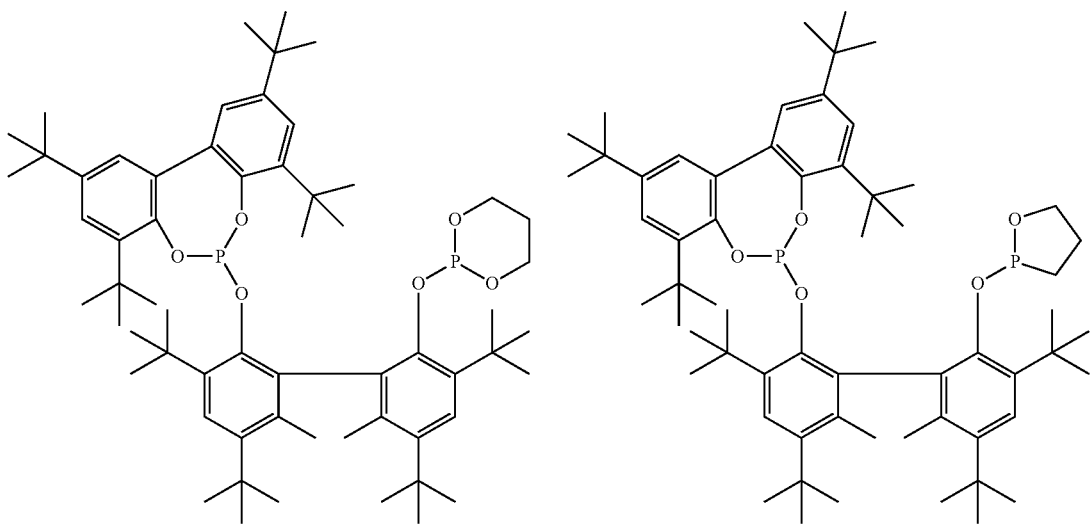

-continued
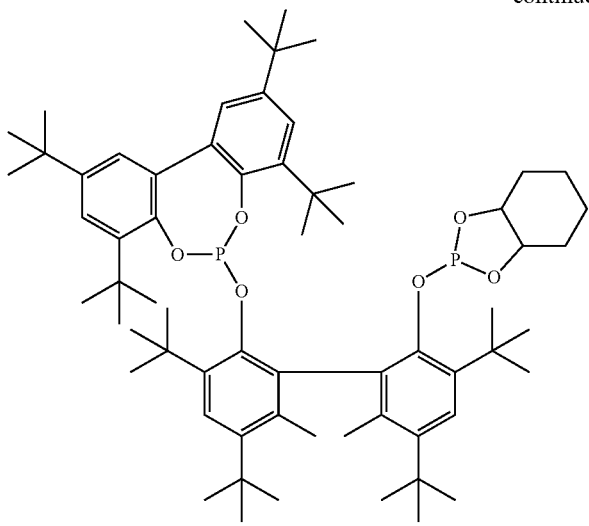
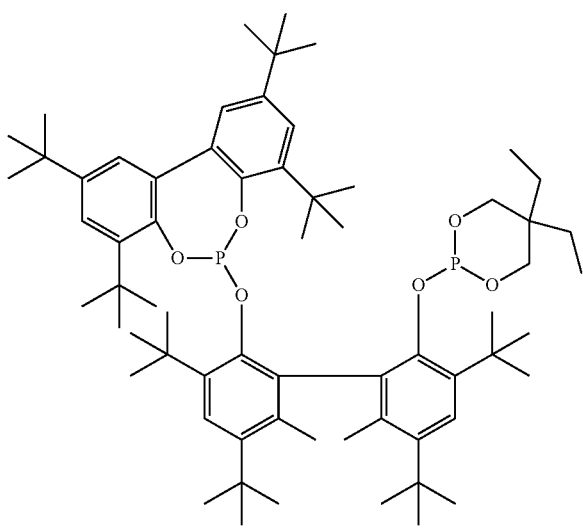
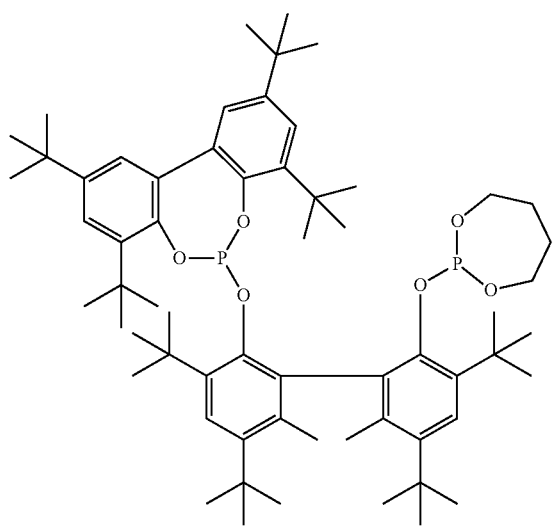
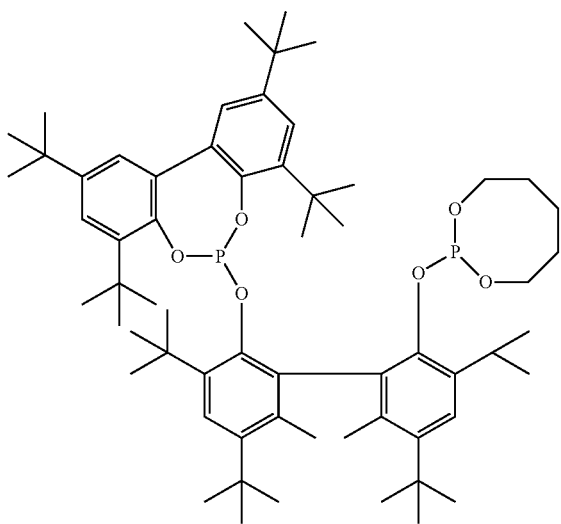 [SMILES: Cc1c(C(C)(C)C)cc(C(C)C)c(OP2OCCCCCO2)c1-c1c(C)c(C(C)(C)C)cc(C(C)(C)C)c1Op1oc2c(C(C)(C)C)cc(C(C)(C)C)cc2c2cc(C(C)(C)C)cc(C(C)(C)C)c2o1]

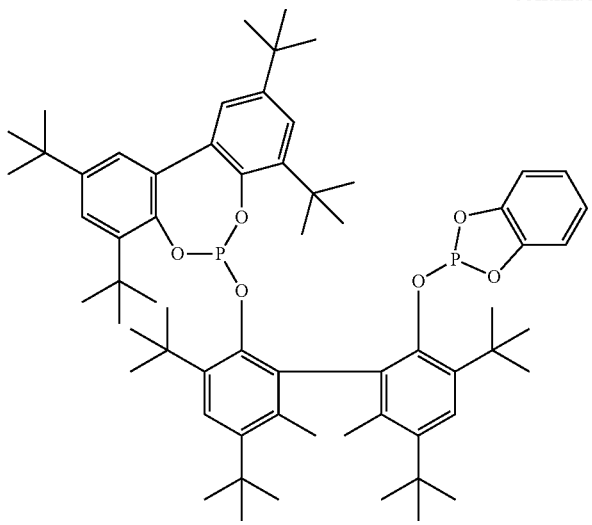
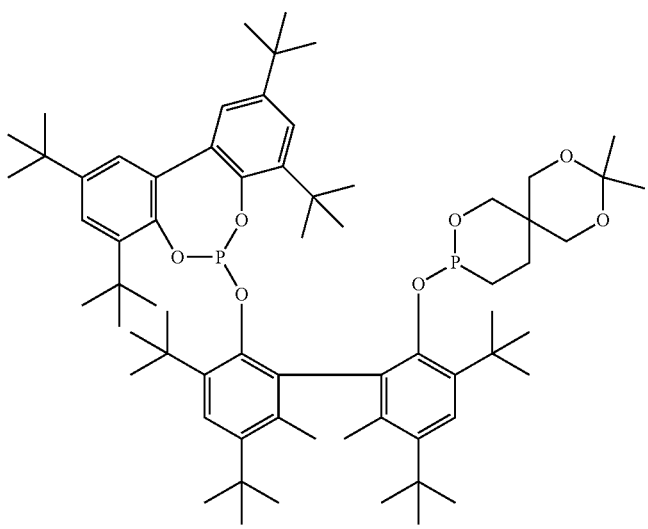
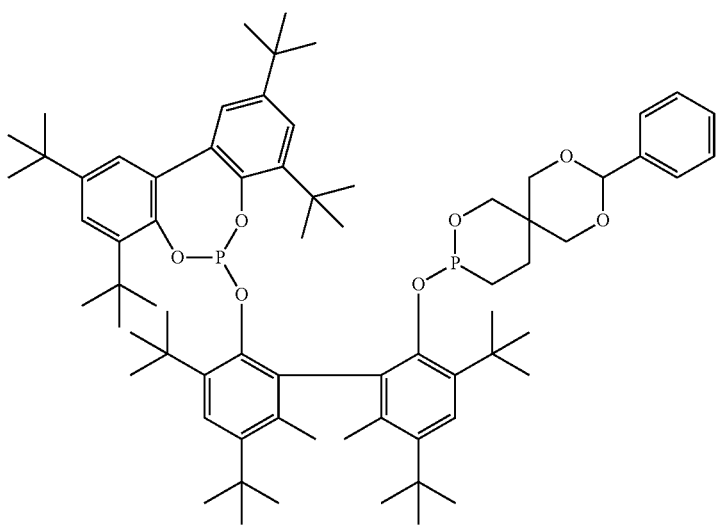

31                                    32
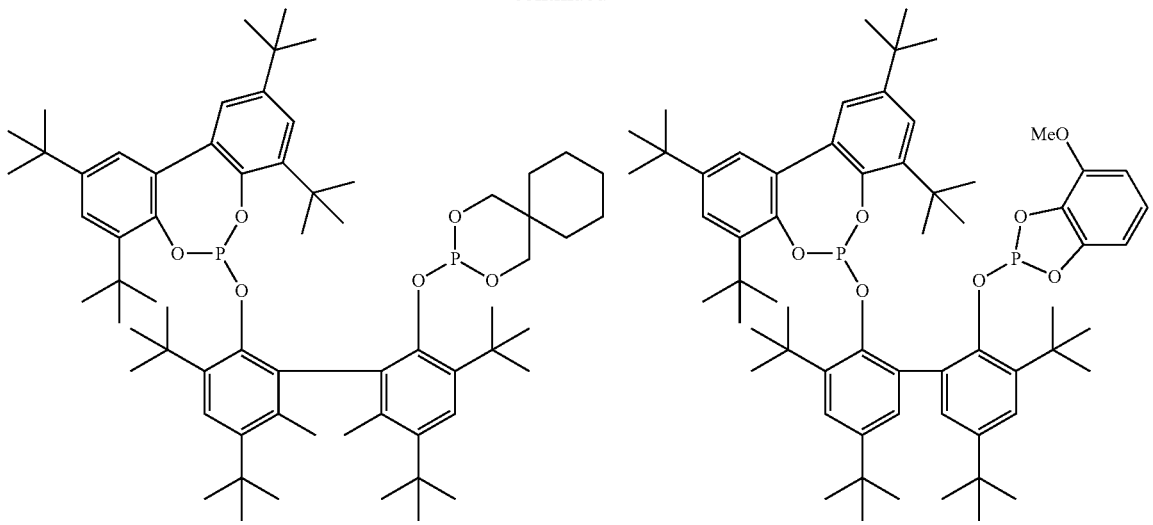
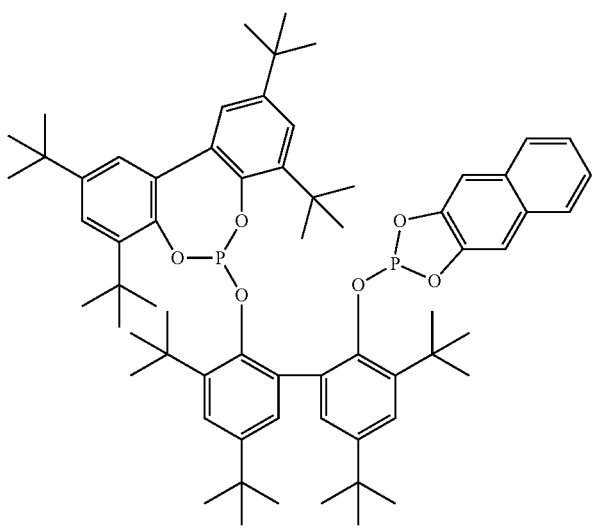
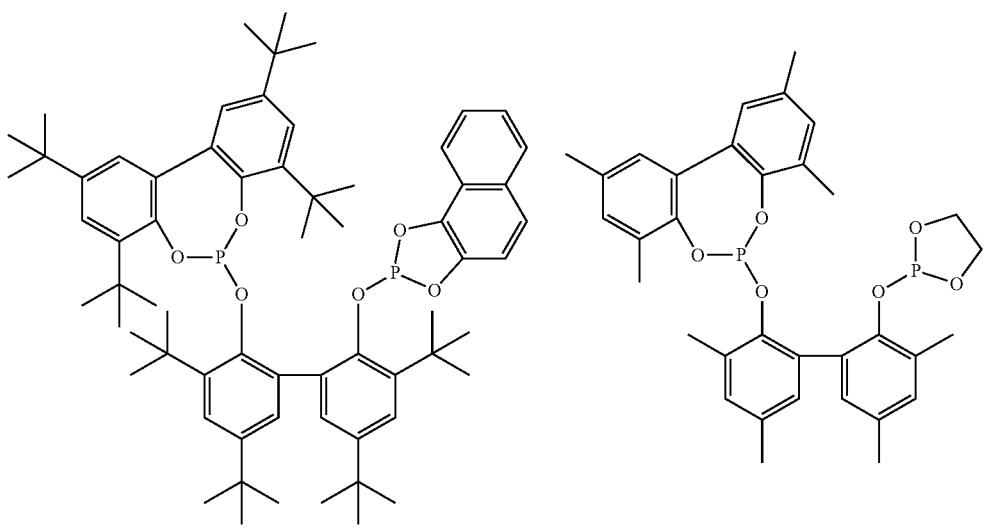

33
34
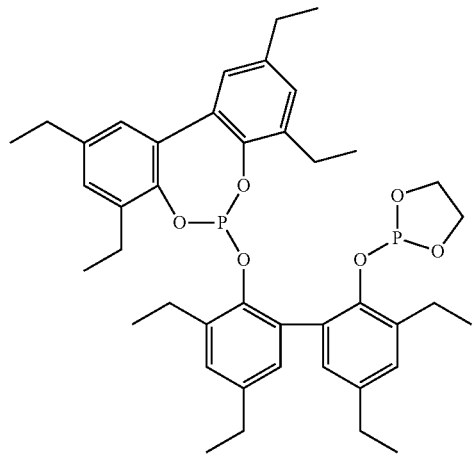
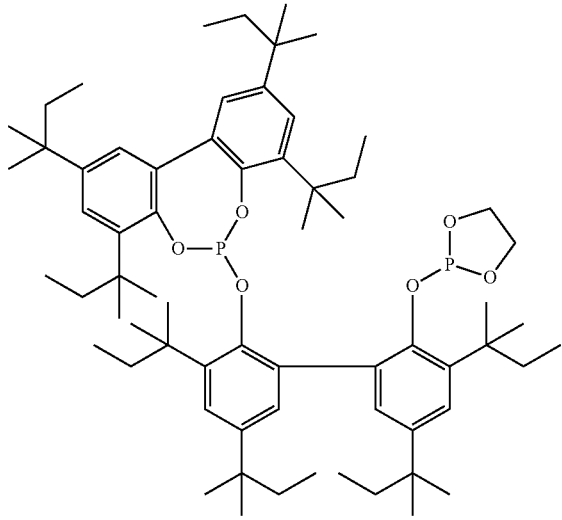
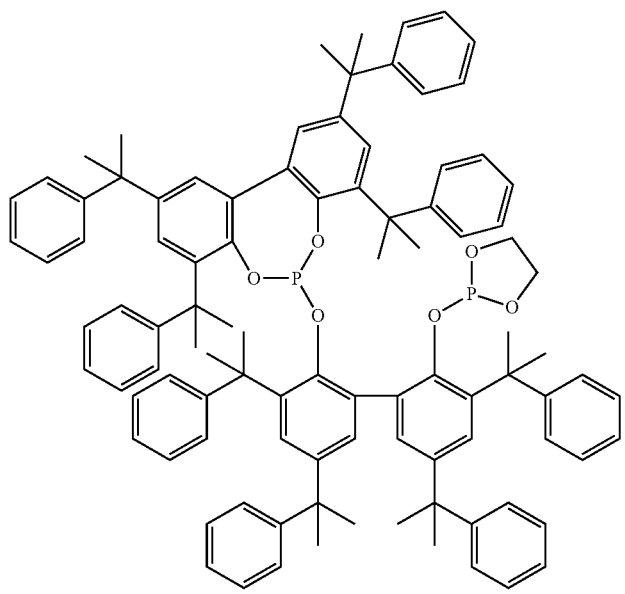
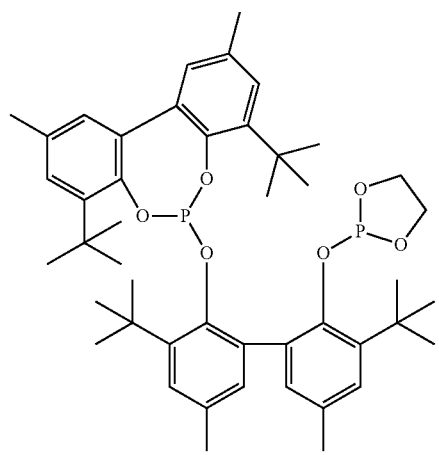
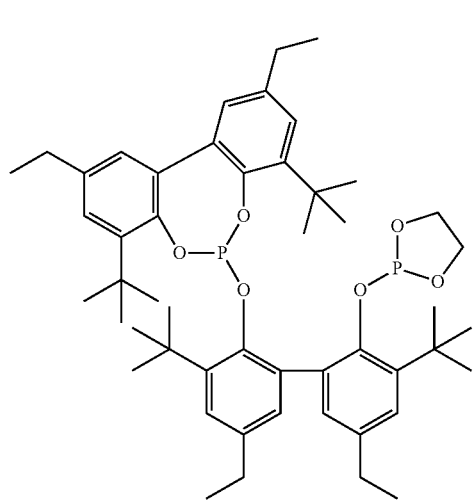
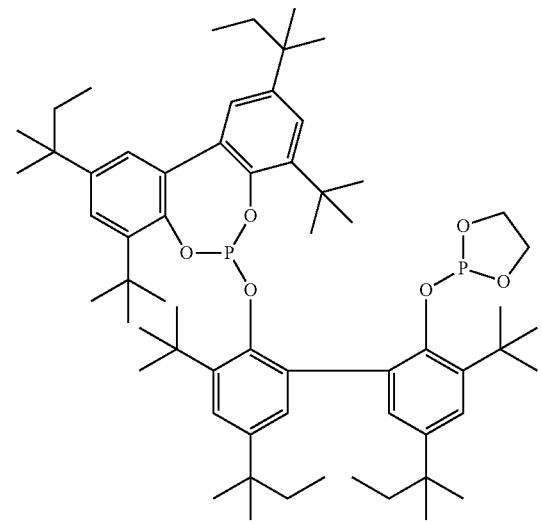

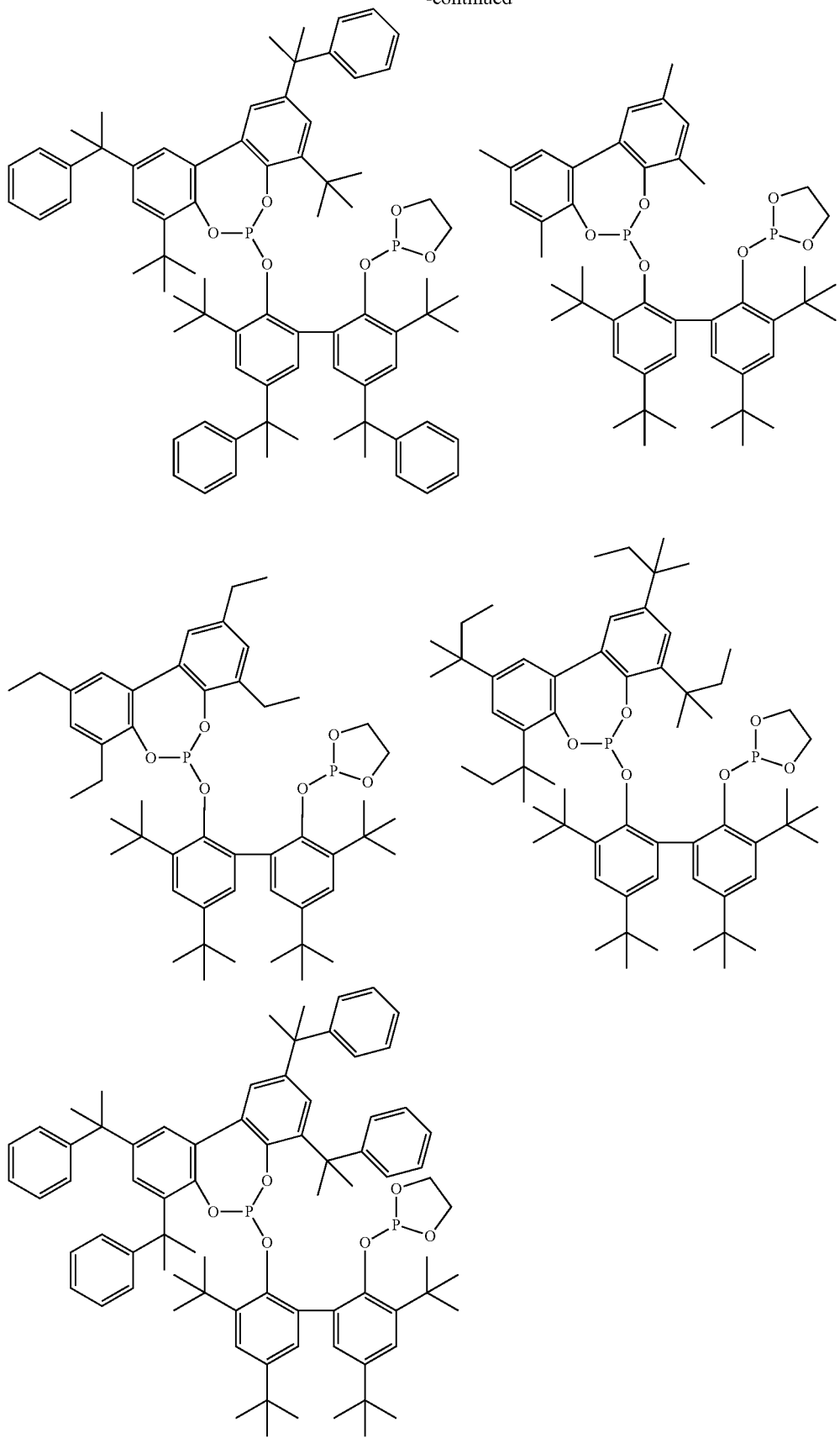

Among the aforementioned ligands, from the viewpoint of reaction rate, the compounds represented by the formula (4) are especially preferred.

Though the use amount of the ligand is not particularly limited, it is preferably in a range of 1 to 1,000 mol, and more preferably in a range of 2 to 500 mol, and from the viewpoint of reaction rate, still more preferably in a range of 3 to 200 mol as expressed in terms of a coordinating atom in the ligand per mol of the metal in the metal compound belonging to the Groups 8 to 10. In the case where the use amount of the ligand is less than 2 mol as expressed in terms of a coordinating atom in the ligand per mol of the metal in the metal compound belonging to the Groups 8 to 10, the stability of the catalyst is impaired, whereas in the case where it is more than 1,000 mol, the reaction rate tends to become low.

The hydroformylation reaction can be performed in the presence or absence of a solvent. Examples of such a solvent include saturated aliphatic hydrocarbons, such as pentane, hexane, heptane, octane, nonane, decane, cyclohexane, etc.; aromatic hydrocarbons, such as benzene, toluene, ethylbenzene, propylbenzene, xylene, ethyltoluene, etc.; alcohols, such as isopropanol, isobutanol, isopentanol, neopentyl alcohol, ethylene glycol, 1,2-propanediol, 1,3-propanediol, 1,2-butanediol, 1,4-butanediol, diethylene glycol, triethylene glycol, etc.; ethers, such as dimethyl ether, ethyl methyl ether, diethyl ether, dipropyl ether, butyl methyl ether, t-butyl methyl ether, dibutyl ether, ethyl phenyl ether, diphenyl ether, tetrahydrofuran, 1,4-dioxane, diethylene glycol dimethyl ether, triethylene glycol dimethyl ether, tetraethylene glycol, dimethyl ether etc.; ketones, such as acetone, ethyl methyl ketone, methyl isopropyl ketone, diethyl ketone, ethyl propyl ketone, dipropyl ketone, etc.; and the like. These solvents may be used alone, or may be used in combination of two or more thereof. In the case of using the solvent, though the use amount of the solvent is not particularly limited, in general, it is preferably in a range of 1 to 90% by mass relative to the whole of the reaction mixture.

A reaction temperature in the hydroformylation reaction is preferably in a range of 40 to 170° C., and from the viewpoint of suppressing the catalyst deactivation, it is more preferably in a range of 50 to 150° C. In addition, a reaction pressure is preferably in a range of 0.01 to 15 MPa (gauge pressure), and more preferably in a range of 0.5 to 10 MPa (gauge pressure). A reaction time is typically in a range of 0.5 to 20 hours, and preferably in a range of 0.5 to 10 hours.

A method for carrying out the hydroformylation reaction is not particularly limited. For example, the acetal compound (2) is charged in the presence of a mixed gas of carbon monoxide/hydrogen of 1/1 (molar ratio), a mixed solution of the ligand, the metal compound belonging to the Groups 8 to 10, and the solvent is fed while stirring, and the contents are allowed to react with each other at a predetermined temperature and a predetermined pressure for a predetermined time.

The reaction can be performed in either a batch mode or a continuous mode using an agitation type reactor, a circulation type reactor, a bubble tower type reactor, or the like. If necessary, the reaction may be carried out by recovering the unreacted acetal compound (2) from the reaction solution after the reaction and recirculating it into the reactor. The continuous mode can be carried out using a single reactor or plural reactors arranged in series or in parallel.

A separation and purification method of the acetal compound (i) from the reaction mixture obtained by the aforementioned method is not particularly limited, and a method which is adopted for usual separation and purification of an organic compound can be adopted. For example, the acetal compound (1) with a high purity can be acquired evaporating the solvent, the basic substance, and the like from the reaction mixture under reduced pressure and then distilling the residue under reduced pressure. In addition, prior to such distillation, by subjecting the residue to a method, such as evaporation, extraction, adsorption, etc., the ligand and the metal compound belonging to the Groups 8 to 10 may be separated. The separated ligand and the metal compound belonging to the Groups 8 to 10 can be again used for the hydroformylation reaction.

(Production of MGL)

Next, a method for obtaining MGL through hydrolysis of the acetal compound (1) is described. MGL can be obtained by allowing the acetal (1) to react with water. The reaction with water may be performed in the absence of catalyst, and if desired, an acid may be used as the catalyst. The acid to be used is not particularly limited, and examples thereof include inorganic acids and salts thereof, such as sulfuric acid phosphoric acid nitric acid, hydrochloric acid, boric acid, etc.; organic acids and salts thereof, such as formic acid, acetic acid, propionic acid, oxalic acid, methanesulfonic acid, p-toluenesulfonic acid, pyridinium p-toluenesulfonate, etc.; solid acids, such as a cation exchange resin, silica alumina, zeolite, activated clay, etc.; and the like.

Though the use amount of the aforementioned acid varies with the kind of the acid used or the amount of water, so far as the case of using hydrochloric acid is concerned, the acid is used in an amount of preferably ranging from 0.0001% by mass to 10% by mass, and more preferably ranging from 0.001% by mass to 5% by mass of the reaction solution. When the use amount of the acid is less than 0.0001% by mass, a sufficient reaction rate is often not obtained, whereas in the case of using the acid in an amount of more than 10% by mass, the use amount of a base on the occasion of neutralization increases, so that a load in a post-treatment process increases.

Though the amount of water to be used is not particularly limited, it is typically 0.1 to 10,000 times by mass, preferably 0.2 to 5,000 times by mass, and more preferably 0.3 to 1,000 times by mass relative to the acetal compound (1). In the case where the amount of water is less than 0.1 times by mass, a sufficient yield is often not obtained, whereas in the case of using water in an amount of more than 10,000 times by mass, the energy necessary for recovery of the target material tends to increase.

The reaction can be performed in the presence or absence of a solvent. Though the solvent to be used is not particularly limited, examples thereof include ethers, such as tetrahydrofuran, diethyl ether, diisopropyl ether, t-butyl methyl ether, methyltetrahydropyran, ethylene glycol dimethyl ether, etc.; aliphatic or aromatic hydrocarbons, such as hexane, heptane, cyclohexane, toluene, xylene, mesitylene, etc.; ketones, such as acetone, methyl isopropyl ketone, methyl isobutyl ketone, etc.; and the like. These may be used alone, or may be used in combination of two or more thereof. The use amount of the solvent is not particularly limited.

Though a reaction time is not particularly limited, it is typically 5 seconds or more, preferably 1 minute or more, and more preferably 10 minutes or more. Though a reaction temperature is not particularly limited, it is typically −20° C. to 350° C., preferably 0° C. to 250° C., and more preferably 10° C. to 100° C.

MGL in the reaction mixture obtained by the aforementioned method can be separated and purified, if desired. The separation and purification method is not particularly limited, and a method which is adopted for usual separation and purification of an organic compound can be adopted. For example, MGL with a high purity can be acquired by evaporating the solvent or an alcohol produced through hydrolysis from the reaction mixture under reduced pressure and then distilling the residue under reduced pressure. In addition, prior to such distillation, by subjecting the residue to a method, such as neutralization, adsorption, washing, etc., the acid may be removed. In order to avoid multimerization, the resulting MGL can also be stored upon dilution with a solvent, such as water, etc., if desired.

EXAMPLES

The present invention is hereunder specifically described by reference to Examples and so on, but it should be construed that the present invention is by no means limited to these Examples.

Example 1: Synthesis of Compound A

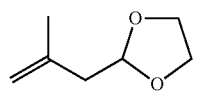

Compound A

In a reactor, 1,390 g of cyclohexane, 618.0 g (9.96 mol) of ethylene glycol, and 0.3 g (3.1 mmol) of sulfuric acid were taken and heated at 90° C. 686.0 g (8.13 mol) of 3-methyl-3-buten-1-al was added dropwise over 4 hours while removing produced water to the outside of the system by means of azeotropic dehydration. After completion of the dropwise addition, the contents were stirred at 90° C. for 1 hour, and the reaction mixture was then cooled to room temperature and neutralized with sodium methoxide. The solvent was evaporated under a reduced pressure from the resulting reaction solution, and the residue was distilled and purified to obtain 969.0 g (7.56 mmol, yield: 92.6%) of the target Compound A.

$^1$H-NMR (400 MHz, CDCl$_3$, TMS) δ: 1.805 (s, 3H), 2.382 (d, 2H), 3.843 to 4.008 (m, 4H), 4.828 (q, 1H), 4.868 (t, 1H), 4.982 (t, 1H)

Example 2: Synthesis of Compound B

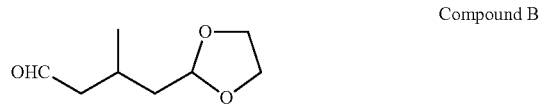

Compound B

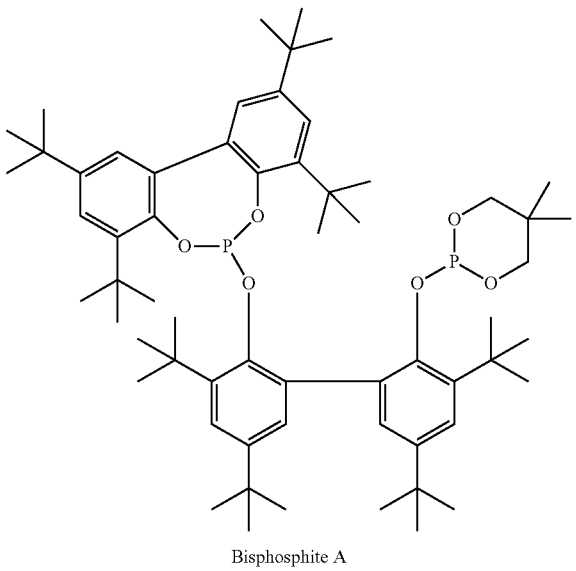 [SMILES: CC1(C)COP(Oc2c(-c3cc(C(C)(C)C)cc(C(C)(C)C)c3Op3oc4c(C(C)(C)C)cc(C(C)(C)C)cc4c4cc(C(C)(C)C)cc(C(C)(C)C)c4o3)cc(C(C)(C)C)cc2C(C)(C)C)OC1]

Bisphosphite A

A solution of 1.08 g of Bisphosphite A and 14.2 mg of Rh(acac)(CO)$_2$ dissolved in 100 mL of toluene was prepared [(rhodium atom)/(phosphorus atom)]=1/20 (molar ratio)). In an electromagnetic agitation type autoclave equipped with a gas introduction port and a sampling port, 45 mL of Compound A and 10 mL of the above-prepared catalyst solution (rhodium compound concentration within the reaction system: 0.1 mmol/L) were added under a nitrogen atmosphere; the pressure within the autoclave was regulated to 8 MPa (gauge pressure) with a mixed gas of carbon monoxide/ hydrogen of 1/1 (molar ratio); thereafter, the temperature within the autoclave was raised to 130° C. while stirring; and the contents were allowed to react for 4 hours. During the reaction, the mixed gas of carbon monoxide/hydrogen of 1/1 (molar ratio) was continually fed to keep the pressure within the reaction system at a fixed level. As a result of analyzing the resulting reaction solution means of gas chromatography, a conversion of Compound A was 90.0%, and a selectivity of Compound B was 97.0%.

Example 3: Synthesis of Compound B

The reaction was carried out in the same manner as in Example 2, except for using 3.56 g of tris(2,4-di-t-butylphenyl) phosphite in place of the Bisphosphite A, to regulate the (rhodium atom)/(phosphorus atom) ratio to 1/100 (molar ratio) and changing the reaction time to 2 hours. A conversion of Compound A was 99.2%, and a selectivity of Compound B was 94.3%.

Example 4: Synthesis of Compound B

The reaction was carried out in the same manner as in Example 2, except for using 1.44 g of triphenylphosphine in place of the Bisphosphite A, to regulate the (rhodium atom)/(phosphorus atom) ratio to 1/100 (molar ratio) and changing the reaction time to 3.5 hours. A conversion of Compound A was 80.0%, and a selectivity of Compound B was 94.1%.

Example 5: Synthesis of MGL

In a three-neck flask, 636.4 mg of 1 mol/L hydrochloric acid (hydrochloric acid: 0.64 mmol, 23.3 mg), 600 mL of distilled water, and 100.8 g (636.9 mmol) of Compound B were charged, and the contents were stirred in a nitrogen atmosphere at 60° C. for 3.5 hours. As a result of analyzing the resulting reaction solution by means of gas chromatography, a conversion of Compound B was 97.2%, and a selectivity of MGL was 99.8%. The reaction solution was cooled to room temperature, then neutralized with sodium hydrogencarbonate, and extracted three times with 600 mL of ethyl acetate. The resulting organic layers were gathered, the solvent was evaporated under reduced pressure, and the residue was then distilled and purified to obtain 65.8 g (576.4 mmol, yield: 90.5%) MGL.

INDUSTRIAL APPLICABILITY

3-Methylglutaraldehyde (MGL) obtained by the present invention is a useful compound as a curing agent for photosensitive material, a tanning agent for leather, and a synthesis intermediate.

The invention claimed is:

1. A production method of 3-methylglutaraldehyde, comprising:
hydrolyzing a compound represented by the following general formula (1):

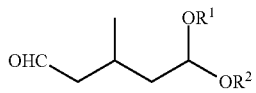
(1)

wherein $R^1$ and $R^2$ each independently represent an alkyl group having 1 to 6 carbon atoms, or are mutually coupled to represent an alkylene group having 2 to 6 carbon atoms.

2. The production method according to claim 1, further comprising:
subjecting a compound represented by the following general formula (2) to hydroformylation to obtain the compound represented by the general formula (1):

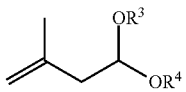
(2)

wherein $R^3$ and $R^4$ each independently represent an alkyl group having 1 to 6 carbon atoms, or are mutually coupled to represent an alkylene group having 2 to 6 carbon atoms.

3. The production method according to claim 2, further comprising:
subjecting 3-methyl-3-buten-1-al to acetalization, to obtain the compound represented by the general formula (2).

4. A compound represented by the following general formula (3):

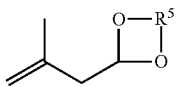
(3)

wherein $R^5$ represents a linear alkylene group having 2 carbon atoms.

5. A compound represented by the following general formula (3):

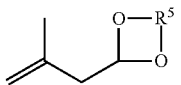
(3)

wherein $R^5$ represents a linear alkylene group having 4-6 carbon atoms.

* * * * *